(12) United States Patent
Zhang

(10) Patent No.: US 10,570,031 B2
(45) Date of Patent: Feb. 25, 2020

(54) HYDROGEN-ENRICHED WATER GENERATOR AND DISPENSER

(71) Applicant: Hongkai Zhang, Shanghai (CN)

(72) Inventor: Hongkai Zhang, Shanghai (CN)

(*) Notice: Subject to any disclaimer, the term of this patent is extended or adjusted under 35 U.S.C. 154(b) by 186 days.

(21) Appl. No.: 15/642,296

(22) Filed: Jul. 5, 2017

(65) Prior Publication Data

US 2018/0009682 A1    Jan. 11, 2018

(30) Foreign Application Priority Data

Jul. 5, 2016  (CN) .......................... 2016 1 0519638

(51) Int. Cl.
| | |
|---|---|
| *C02F 1/461* | (2006.01) |
| *C02F 1/48* | (2006.01) |
| *C02F 1/28* | (2006.01) |
| *A61K 33/00* | (2006.01) |
| *B67D 1/00* | (2006.01) |
| *B67D 1/08* | (2006.01) |

(52) U.S. Cl.
CPC ............ *C02F 1/4618* (2013.01); *A61K 33/00* (2013.01); *B67D 1/0004* (2013.01); *B67D 1/0884* (2013.01); *C02F 1/288* (2013.01); *C02F 1/48* (2013.01); *C02F 1/281* (2013.01); *C02F 1/283* (2013.01); *C02F 1/286* (2013.01)

(58) Field of Classification Search
CPC .......... C02F 1/4618; C02F 1/288; C02F 1/48; C02F 1/281; C02F 1/283; C02F 1/286; A61K 33/00; B67D 1/0004; B67D 1/0884
See application file for complete search history.

(56) References Cited

U.S. PATENT DOCUMENTS

2016/0257575 A1* 9/2016 Hawes ................... B01D 39/14
2016/0330968 A1* 11/2016 Owens .................. H01L 31/042

* cited by examiner

*Primary Examiner* — Ciel P Thomas
(74) *Attorney, Agent, or Firm* — Novoclaims Patent Services LLC; Mei Lin Wong

(57) ABSTRACT

A hydrogen-enriched water generator and dispenser includes a main casing, a hydrogen water generator supported in the main casing, and a water tank. The hydrogen water generator includes a magnetic field generator and an electrode arrangement supported in the main casing. The water tank is adapted for storing a predetermined amount of regular water. The magnetic field generator is arranged to deliver electromagnetic wave having ultra-long wavelength to the regular water stored in the water tank upon electrolyzing and ionizing by the electrode arrangement, so that the regular water is electrolyzed and ionized to contain a predetermined amount of hydrogen ions for direct consumption.

2 Claims, 6 Drawing Sheets

HYDROGEN-ENRICHED WATER GENERATOR AND DISPENSER

CROSS REFERENCE OF RELATED APPLICATION

This application claimed priority of a foreign application number 201610519638.5 with a filing date of Jul. 5, 2016 in China. The contents of these specifications, including any intervening amendments thereto, are incorporated herein by reference.

BACKGROUND OF THE PRESENT INVENTION

Field of Invention

The present invention relates to a drinking water apparatus, and more particularly to a hydrogen-enriched water generator and dispenser which is capable of conveniently producing water having a rich mix of hydrogen molecules.

Description of Related Arts

Quantum represents a minimum amount of any physical entity in an interaction. Quantum mechanics is a branch of physics which is a fundamental theory of nature at small scales and low energies of atoms and subatomic particles. On the other hand, hydrogen-enriched water has recently been developed to provide an alternate form of water. Hydrogen water may be referred to as a solution of hydrogen molecules $H_2$ in water. The function of hydrogen-enriched water is to provide hydrogen that is easier for human cells to use.

Conventional biology and chemistry reveal that a diameter of a human cell membrane is approximately 2 nm. As a result, anything larger than that may not enter the cells. Hydrogen is extremely unique since it has the capability to act at the cellular level. Hydrogen is small enough to enter human cells, such as blood brain barriers, mitochondria, and even has the ability to translocate to the nucleus under certain conditions. Once in these ideal locations of the cell, hydrogen may exert antioxidant, anti-apoptotic, anti-inflammatory, and cytoprotective properties that are beneficial to the cell.

Quantum medicine is a branch of complementary medicine that uses a controlled amount of electromagnetic radiation in the treatment, diagnosis, and prevention of certain diseases. Quantum energy may benefit human body in a number of ways. (1) Quantum energy may activate molecular activity. (2) By activating molecular activities in human's cells, quantum energy may substantially improve metabolism, immune system, and balance and recovery ability of human body. (3) Quantum energy may improve the overall blood circulation of a human body. Quantum energy may cause blood vessel to dilate, and therefore increase blood flow to every part of the human body. (4) Quantum energy may be anti-inflammation and help human body to fight against bacteria. (5) Quantum energy may also help in reducing pain because it may reduce the sensitivity of peripheral nerves.

Hydrogen has very high permeability. The major cause of ageing is DNA oxidation. Oxidation of human cell may also cause high blood pressure, high in fat, and high blood sugar. When hydrogen atoms combine with $O^+$, the resulting product is $H_2O$ (i.e. water). When hydrogen atoms enters human cells, it may flush away toxic or harmful substances in human cells.

A major disadvantage of convention hydrogen-enriched water generator and dispensers is that they are generally instable and complicated to use. When hydrogen molecules are added to water, they escape or evaporate very rapidly because hydrogen molecules, if uncombined with other elements, are very unstable. As a result, hydrogen-enriched water must be consumed shortly after they have been produced. Conventional method and apparatus for producing hydrogen-enriched water do not generally allow users to have access to the hydrogen-enriched water when is produced. As a result, hydrogen-enriched water must be sealed and transported from the point of production to reach consumers. This increases the cost of consuming hydrogen-enriched water.

Moreover, conventional hydrogen-enriched water generator and dispensers do not utilize quantum energy as a method to produce hydrogen-enriched water.

As a result, there is a need to develop a hydrogen-enriched water generator and dispenser which is easily and convenient to use. The hydrogen-enriched water thus produced has the maximum effectiveness compared to conventional hydrogen-enriched water.

SUMMARY OF THE PRESENT INVENTION

Certain variations of the present invention provide a hydrogen-enriched water generator and dispenser which is capable of conveniently producing water having a rich mix of hydrogen molecules.

Certain variations of the present invention provide a hydrogen-enriched water generator and dispenser which utilizes quantum energy as a method for producing hydrogen-enriched water in a very stable manner.

Certain variations of the present invention provide a hydrogen-enriched water generator and dispenser which may allow users to obtain hydrogen-enriched water in a very convenient and domestic environment. As a result, users of the present invention may drink hydrogen-enriched water whenever necessary.

In one aspect of the present invention, it provides a hydrogen-enriched water generator and dispenser, comprising:

a main casing;

a hydrogen water generator supported in the main casing, the hydrogen water generator comprising a magnetic field generator and a electrode arrangements supported in the main casing; and a water tank supported by the main casing, the water tank being adapted for storing a predetermined amount of regular water, the magnetic field generator being arranged to deliver ultra-long electromagnetic wave to the regular water stored in the water tank upon electrolyzing and ionizing by the electrode arrangement, so that so that the regular water is electrolyzed and ionized to contain a predetermined amount of hydrogen ions for direct consumption.

In another aspect of the present invention, it provides a method of manufacturing filter elements for use in a hydrogen-enriched water generator and dispenser, comprising the steps of:

(a) mixing a predetermined amount of ammonium sulfate into a predetermined amount of water until the ammonium sulfate dissolves in the water to form a first mixture;

(b) mixing a predetermined amount of maifan stone and a predetermined amount of diatomaceous earth into the first mixture to form a second mixture, and performing hydrolysis of the second mixture at approximately 45° C. to 65° C. for approximately 5 hours to 35 hours to form a third mixture;

(c) mixing a predetermined amount of active carbon, a predetermined amount of aluminum oxide, and a predetermined amount of potassium phosphate into the third mixture to form a fourth mixture;

(d) crystalizing the fourth mixture at approximately 85° C. to 150° C. for approximately 12 hours to 50 hours to form a predetermined amount of core crystal; and (e) heating the core crystal, a predetermined amount of palm fiber, and a predetermined amount of silk fiber in a furnace at approximately 45° C. to 60° C. for approximately 2 hours to 5 hours to form the filter elements 52.

This summary presented above is provided merely to introduce certain concepts and not to identify any key or essential features of the claimed subject matter.

DETAILED DESCRIPTION OF THE PREFERRED EMBODIMENT

Figure 1:
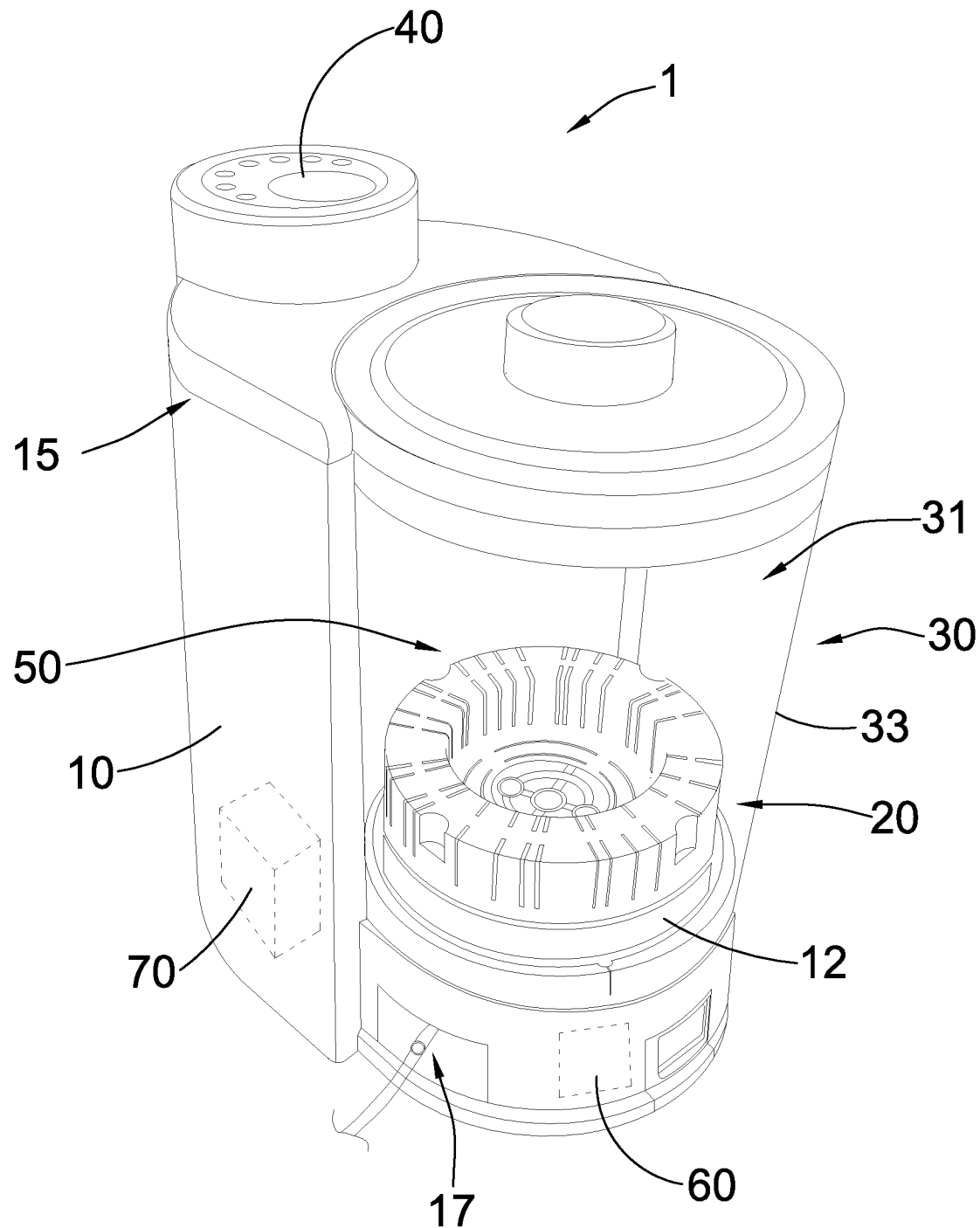
FIG. 1 is a perspective view of a hydrogen-enrich water generator according to a preferred embodiment of the present invention.
Figure 2:
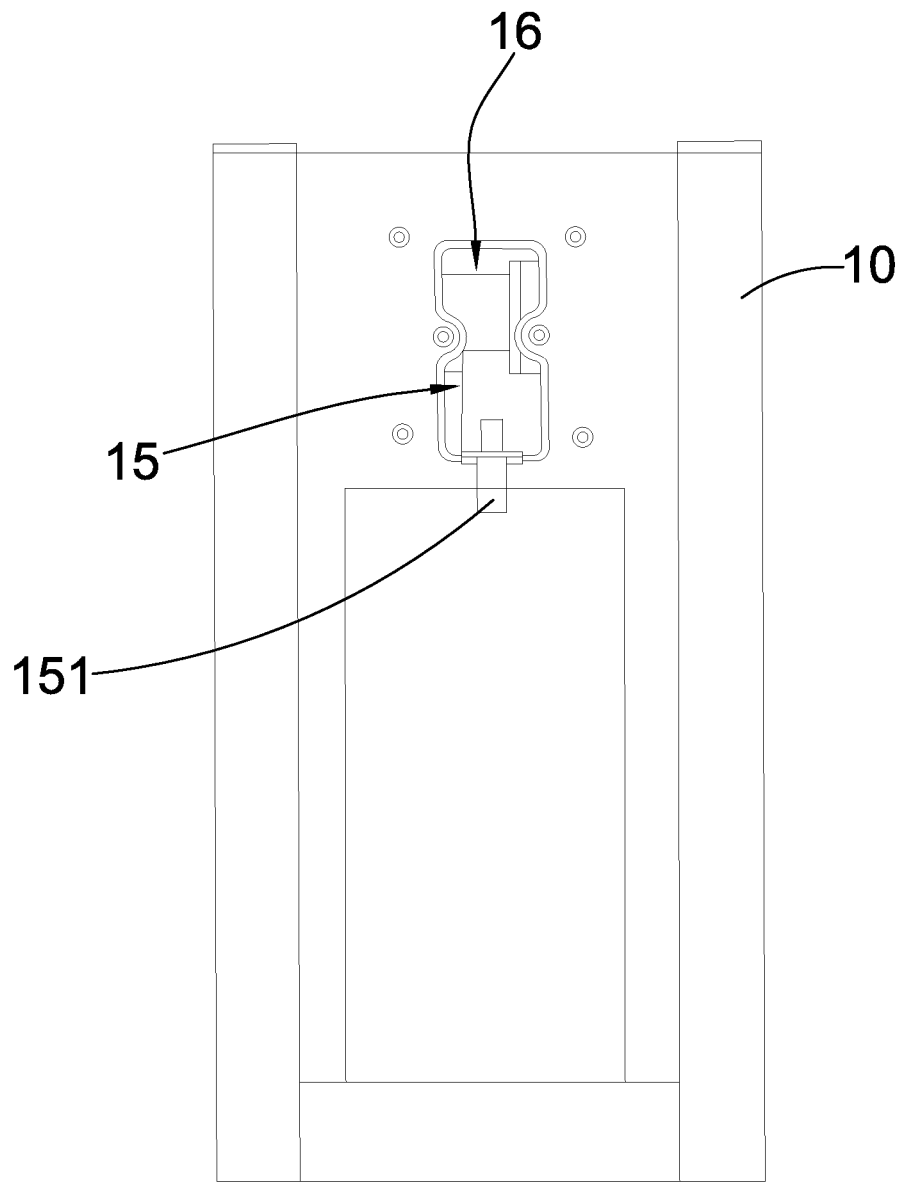
FIG. 2 is a front schematic view of the hydrogen-enrich water generator according to the preferred embodiment of the present invention.
Figure 3:
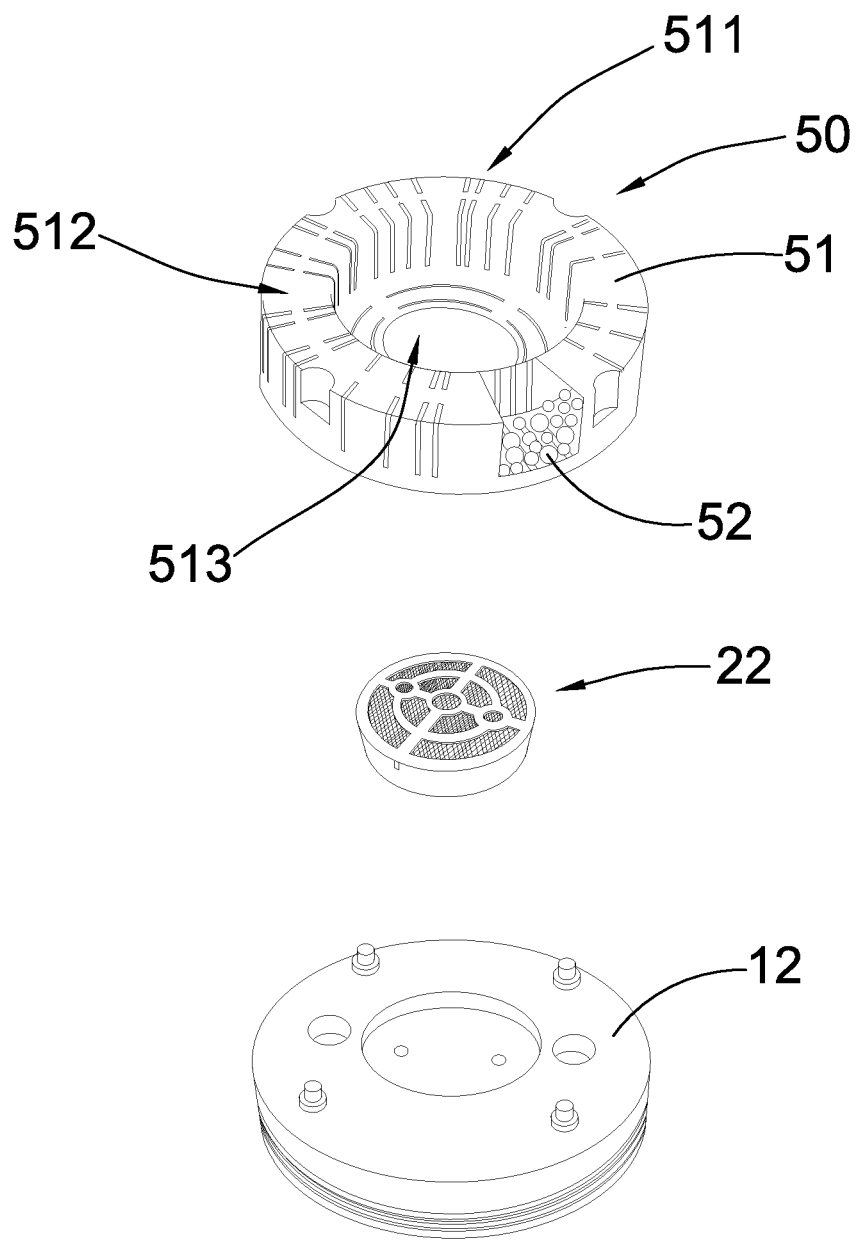
FIG. 3 is a perspective view of an electrode arrangement of the hydrogen-enrich water generator according to the preferred embodiment of the present invention.

The following detailed description of the preferred embodiment is the preferred mode of carrying out the invention. The description is not to be taken in any limiting sense. It is presented for the purpose of illustrating the general principles of the present invention.

Referring to FIG. 1 to 6 of the drawings, a hydrogen-enriched water generator and dispenser 1 according a preferred embodiment of the present invention is illustrated. Broadly, the hydrogen-enriched water generator and dispenser 1 may comprise a main casing 10, a hydrogen water generator 20, and a water tank 30. The hydrogen-enriched water generator and dispenser 1 is for producing a predetermined amount of hydrogen-enriched water in a typical domestic environment.

The hydrogen water generator 20 may be supported in the main casing 10, and may comprise a magnetic field generator 21 and an electrode arrangement 22.

The water tank 30 may be supported by the main casing 10. The water tank 30 may have a water compartment 31 which may be adapted for storing a predetermined amount of regular water. The magnetic field generator 21 may be arranged to deliver ultra-long electromagnetic wave to the regular water stored in the water tank upon electrolyzing and ionizing by the electrode arrangement 22, so that the regular water is electrolyzed and ionized to contain a predetermined amount of hydrogen ions for direct consumption.

According to the preferred embodiment of the present invention, the main casing 10 may have a receiving cavity 16 and may support the hydrogen water generator 20. The main casing 10 may further have a flat bottom surface 11 for stably resting on an external flat surface, such as on a table. Thus, the hydrogen-enriched water generator and dispenser 1 may form a self-contained unit which may stand on a flat surface in a very stable manner. As shown in FIG. 1 of the drawings, the main casing 10 may have a supporting platform 12. The water tank 30, the magnetic field generator 21 and the electrode arrangement 22 may be supported above the supporting platform 12.

In addition, the main casing 10 may have a water dispensing compartment 15 formed on an upper portion of the main casing 10, wherein water stored in the water tank 30 may be guided and pumped to be discharged out of the hydrogen-enriched water generator and dispenser 1 through the water dispensing compartment 15 and a water dispensing outlet 151 (described below in more details). The main casing 10 may further have a water inlet 17 formed on a bottom portion thereof. The water inlet 17 may communicate with the water compartment 31 of the water tank 30 through at least one water pipe.

The hydrogen-enriched water generator and dispenser 1 may further comprise a control panel 40 supported on the main casing 10 at a position on top of the water dispensing compartment 15, wherein a user may select the type of water outputted by the hydrogen-enriched water generator and dispenser 1 (such as regular water, hydrogen-enriched water etc.).

The water tank 30 may comprise a tank body 33 which may be cylindrical in shape, wherein the water compartment 31 may be formed in the tank body 33. The tank body 33 may further has a top opening 34 and a bottom opening 35. The bottom opening 35 may communicate the water compartment 31 with the supporting platform 12 of the main casing 10. The electrode arrangement 22 of the hydrogen water generator 20 may be provided on the supporting platform 12 and accommodated in the water compartment 31 through the bottom opening 35. As such, the hydrogen water generator 20 may be in direct contact with the water stored in the water compartment 31 so as to convert the water in the water compartment 31 from regular water to hydrogen-enriched water through the use of electromagnetic radiation having ultra-long wavelength and the electrode arrangement 22.

The hydrogen-enriched water generator and dispenser 1 may further comprise a filter core 50 provided in the water compartment 31 for communicating with the water stored therein. Specifically, the filter core 50 may comprise a filter casing 51 and a plurality of filter elements 52 received in the filter casing 51. The filter casing 51 may have a plurality of communicating slots 511 for communicating the filter elements 52 with the water received in the water compartment 31. The filter casing 51 may be configured to have a ring-shaped structure having a peripheral housing portion 512 and a central opening 513. The filter elements 52 may be accommodated in the peripheral housing portion 512 and the communicating slots 511 may also be formed on the peripheral housing portion 512 so that water in the water compartment 31 may communicate with the filter elements 52 through the communicating slots 511. Overall speaking, the filter core 50 may have a substantially circular cross sectional shape having a diameter slightly less than that of the water compartment 31 so as to be fittedly accommodated the water compartment 31.

The filter elements 52 may comprise, in percentage by weight, approximately 12.5% to 17.7% of maifan stone, approximately 11.3% to 11.8% of diatomaceous earth, approximately 11.3% to 14.5% of active carbon, approximately 11.3% to 11.8% of aluminum oxide, approximately 9.7% to 14.5% of potassium phosphate, approximately 9.2% to 11.3% of palm fiber, approximately 11.85% to 14.5% of ammonium sulfate, and approximately 12.9% to 13.8% of silk fiber.

In this preferred embodiment of the present invention, the filter elements 52 may comprise, in percentage by weight, approximately 17.7% of maifan stone, approximately 11.3% of diatomaceous earth, approximately 11.3% of active carbon, approximately 11.3% of aluminum oxide, approximately 9.7% of potassium phosphate, approximately 11.3% of palm fiber, approximately 14.5% of ammonium sulfate, and approximately 12.9% of silk fiber.

The filter elements 52 described above may be manufactured by the following steps:

(a) mixing a predetermined amount of ammonium sulfate into a predetermined amount of water until the ammonium sulfate dissolves in the water to form a first mixture;

(b) mixing a predetermined amount of maifan stone and a predetermined amount of diatomaceous earth into the first mixture to form a second mixture, and performing hydrolysis of the second mixture at approximately 45° C. to 65° C. for approximately 5 hours to 35 hours to form a third mixture;

(c) mixing a predetermined amount of active carbon, a predetermined amount of aluminum oxide, and a predetermined amount of potassium phosphate into the third mixture to form a fourth mixture;

(d) crystalizing the fourth mixture at approximately 85° C. to 150° C. for approximately 12 hours to 50 hours to form a predetermined amount of core crystal; and (e) heating the core crystal, a predetermined amount of palm fiber, and a predetermined amount of silk fiber in a furnace at approximately 450° C. to 600° C. for approximately 2 hours to 5 hours to form the filter elements 52.

According to the preferred embodiment of the present invention, the filter elements 52 described above may be manufactured by the following optimal values. In step (b), the hydrolysis of the second mixture may be performed at approximately 45° C. for approximately 5 hours to form the third mixture.

In step (d), the crystallization process may be performed at approximately 85° C. for approximately 12 hours to form the core crystal.

In step (e), the core crystal, the palm fiber, and the silk fiber may be heated in the furnace at approximately 450° C. for approximately 2 hours to form the filter elements 52.

Figure 4:
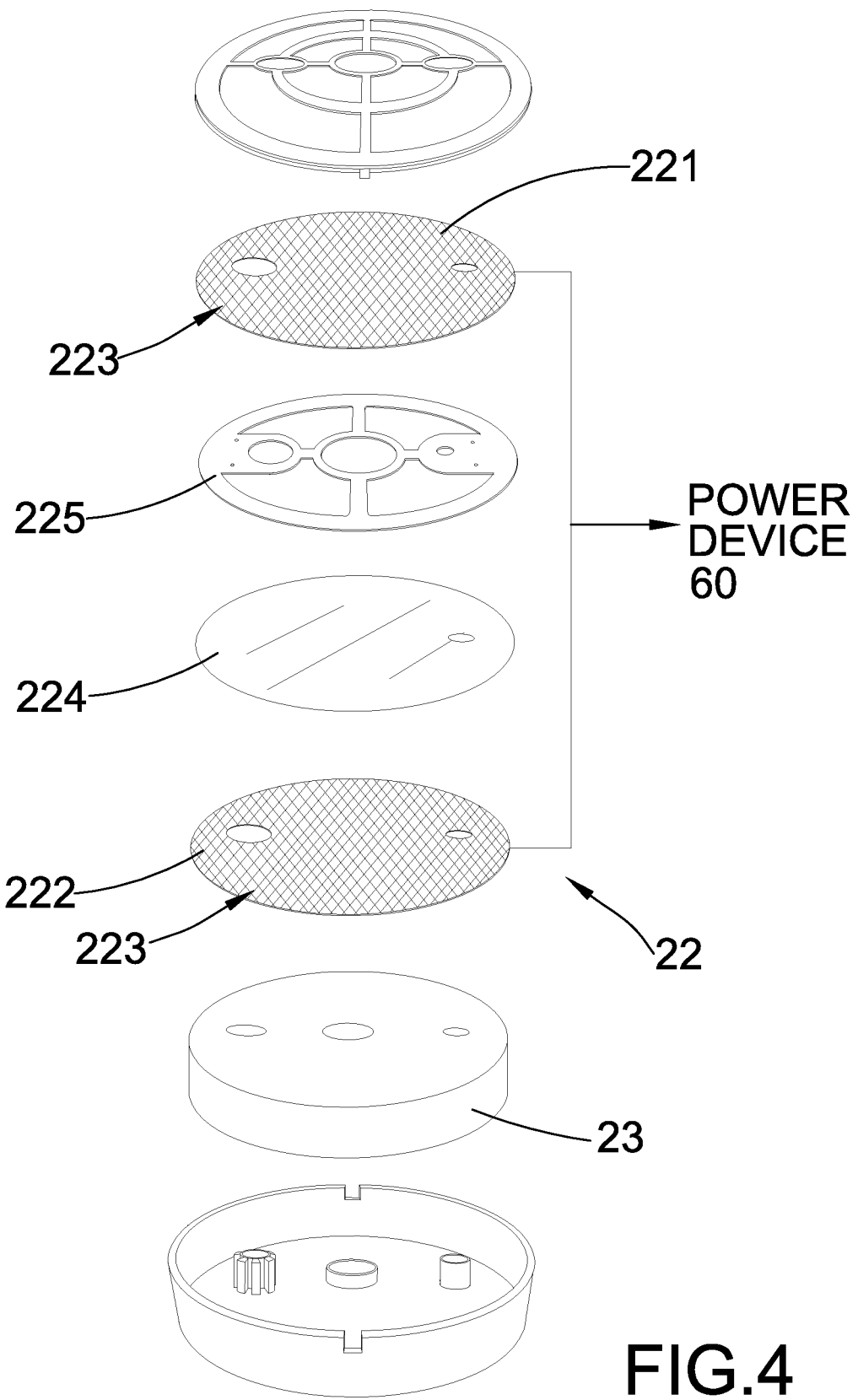
FIG. 4 is an exploded perspective view of the electrode arrangement of the hydrogen-enrich water generator according to the preferred embodiment of the present invention.
Figure 5:
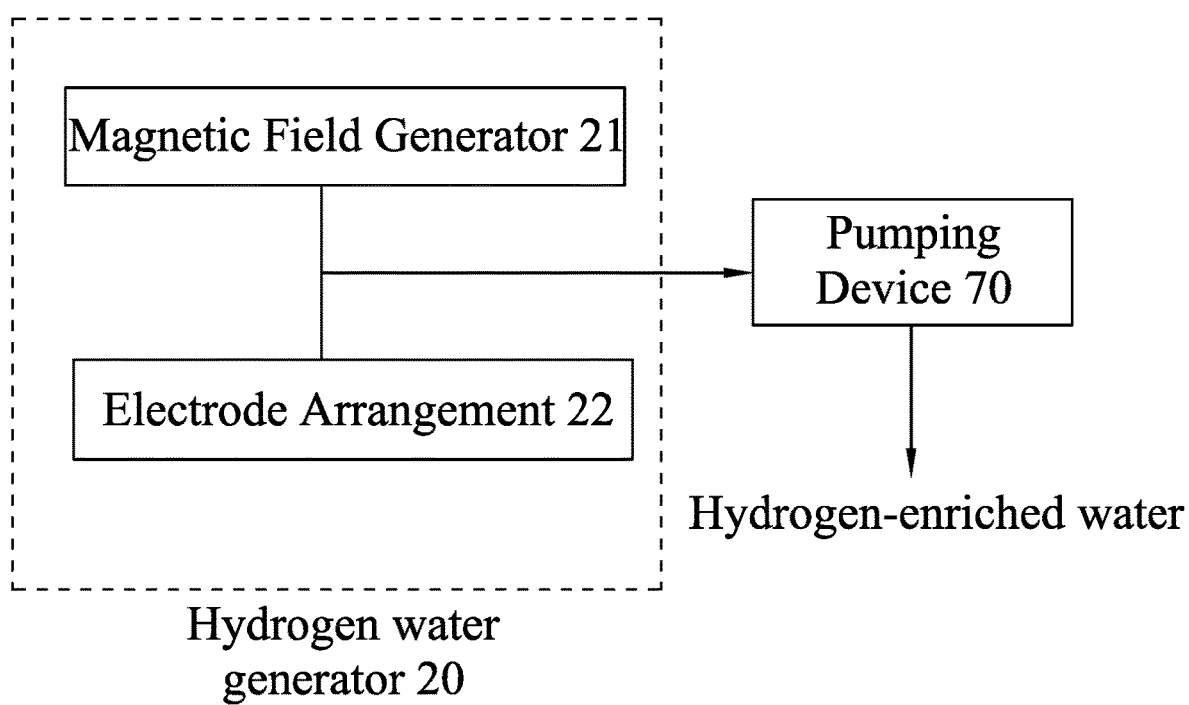
FIG. 5 is a block diagram of a hydrogen water generator of the hydrogen-enrich water generator according to the preferred embodiment of the present invention.
Figure 6:
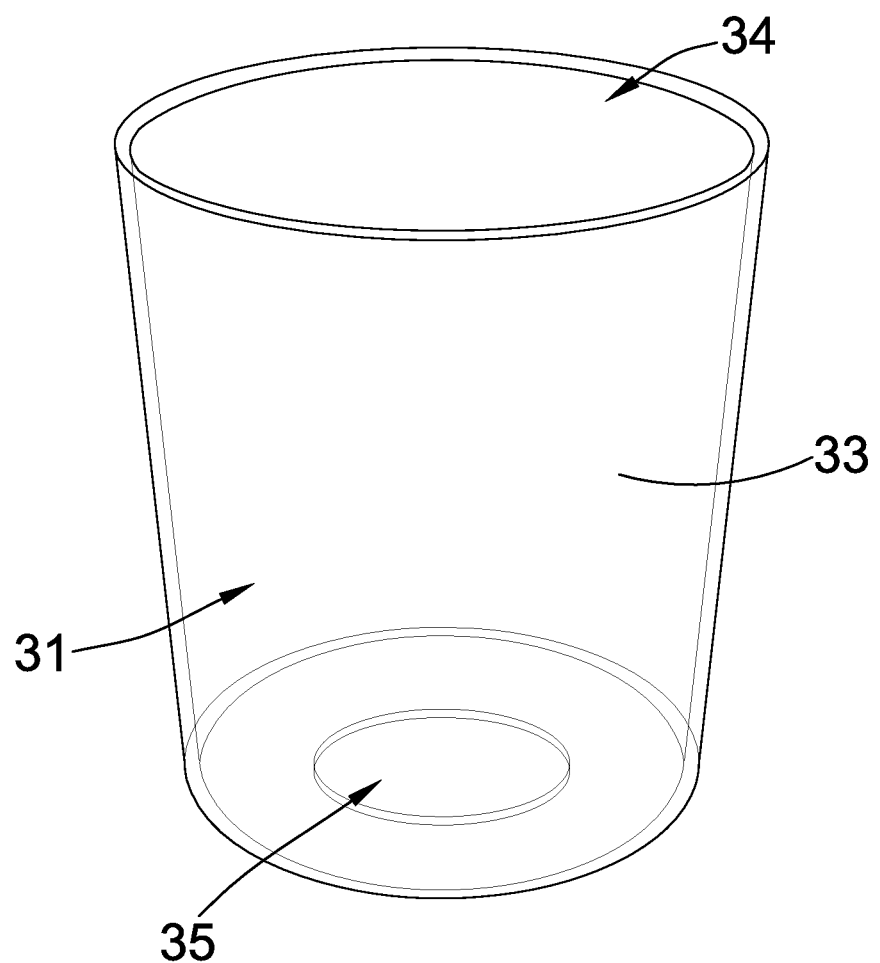
FIG. 6 is a schematic diagram of a water tank of the hydrogen-enrich water generator according to the preferred embodiment of the present invention.

As shown in FIG. 4 of the drawings, the electrode arrangement 22 of the hydrogen water generator 20 may comprise a positive electrodes plates 221 and a negative electrode plate 222 provided underneath the filter core 50 at a position corresponding to the central opening 513 of the filter casing 51. The positive electrode plate 221 and the negative electrode plate 222 may be electrically connected to a positive terminal and a negative terminal of a power source respectively so that the positive electrode plate 221 and the negative electrode plate 222 may form a positive terminal and a negative terminal for electrolyzing the water in the water compartment 31. Each of the positive electrode plate 221 and the negative electrode plate 222 may have a circular peripheral shape and may have a plurality of through meshes 223 formed thereon for allowing water to pass through the corresponding positive electrode plate 221 and the negative electrode plate 222.

Thus, the hydrogen-enriched water generator and dispenser 1 may further comprise a power device 60 provided in the main casing 10 and electrically connected between an external power source and the electrode arrangement 22 for providing positive polarity to the positive electrode plate 221 and negative polarity to the negative electrode plate 222. The power device 60 may also provide electrical power to other components of the hydrogen-enriched water generator and dispenser 1.

Furthermore, the electrode arrangement 22 may further comprise an insulating layer 224 and an insulating frame 225 positioned between the positive electrode plate 221 and the negative electrode plate 222 for preventing electrical conduction between the positive electrode plate 221 and the negative electrode plate 222.

The hydrogen water generator 20 may further comprise a carbon cartridge 23 provided underneath the electrode arrangement 22 for facilitating effective electrolysis of the water stored in the water compartment 31. The carbon cartridge 23 may be configured as having an annular structure which is sized and shaped to correspond to the electrode arrangement 22 so that the carbon cartridge 23 may also be securely supported by the supporting platform 12.

The hydrogen water core 21 of the hydrogen water generator 20 may be provided in the main casing 10 and may be configured to generate electromagnetic wave having ultra-long wavelength, wherein the electromagnetic wave may be transmitted to the water stored in the water compartment 31.

The hydrogen-enriched water generator and dispenser 1 may further comprise a pumping device 70 provided in the main casing and electrically connected to the power device 60 for pumping water from the water compartment 31 to the water dispensing portion 15 through the supporting platform. Hydrogen-enriched water may be pumped from the water compartment 31 to be dispensed out of the main casing 10 in the water dispensing portion 15, preferably through a plurality of tubes 18 connecting the hydrogen water generator 20 and the water dispensing portion 15.

The operation of the present invention may be as follows: a user may use the hydrogen-enriched water generator and dispenser 1 of the present invention to selectively acquire regular water, heated water or hydrogen-enriched water by operating on the control panel 40. When regular water is desired, the user may simply press on the control panel 40 and water may be drawn from the water compartment 31 or directly from an external water source and dispensed from the water dispensing portion 15 and the water dispensing outlet 151.

When the user would like to have hydrogen-enriched water, he may simply need to operate on the control panel 40. Water in the water compartment 31 may be electrolyzed and may communicate with the magnetic field generator 21 so that water in the water compartment 31 may be subject to the exposure of ultra-long electromagnetic wave and eventually pumped to the water dispensing portion 15 for being discharged out of the hydrogen-enriched water generator and dispenser 1 through the water dispensing outlet 151.

As an alternative mode of the hydrogen-enriched water generator and dispenser, the filter elements 52 may comprise, in percentage by weight, approximately 12.9% of maifan stone, approximately 12.2% of diatomaceous earth, approximately 14.8% of active carbon, approximately 12.2% of aluminum oxide, approximately 13.9% of potassium phosphate, approximately 9.6% of palm fiber, approximately 12.2% of ammonium sulfate, and approximately 12.2% of silk fiber.

In the first alternative mode, the filter elements 52 may be manufactured by the following optimal parameters. In step (b), the hydrolysis of the second mixture may be performed at approximately 58° C. for approximately 27 hours to form the third mixture.

In step (d), the crystallization process may be performed at approximately 135° C. for approximately 36 hours to form the core crystal.

In step (e), the core crystal, the palm fiber, and the silk fiber may be heated in the furnace at approximately 535° C. for approximately 4 hours to form the filter elements 52'.

It is worth mentioning that the hydrogen-enriched water generator and dispenser has a compact structure which can be used as a personal hydrogen-enriched water generator and dispenser at home or in an office. According to the preferred embodiment, the size of the device is just about the size of a personal coffee maker which make it possible to bring this hydrogen-enriched water to household use level and personal use level.

The present invention, while illustrated and described in terms of a preferred embodiment and several alternatives, is not limited to the particular description contained in this specification. Additional alternative or equivalent components could also be used to practice the present invention.

What is claimed is:

1. A hydrogen-enriched water generator and dispenser, comprising:
   a main casing;
   a hydrogen water generator supported in said main casing, said hydrogen water generator comprising a magnetic field generator and an electrode arrangement supported in said main casing;
   a water tank supported by said main casing, said water tank being adapted for storing a predetermined amount of regular water, said magnetic field generator being arranged to deliver electromagnetic wave having ultra-long wavelength to said regular water stored in said water tank upon ionizing and electrolyzing by said electrode arrangement, so that said regular water is electrolyzed and ionized to contain a predetermined amount of hydrogen ions for direct consumption; and
   a filter core,
   wherein said main casing has a supporting platform, said water tank, said magnetic field generator and said electrode arrangement being supported above said supporting platform,
   wherein said water tank comprises a tank body having a water compartment, said tank body having a top opening and a bottom opening, said bottom opening communicating said water compartment with said supporting platform of said main casing, said electrode arrangement being provided on said supporting platform and accommodated in said water compartment through said bottom opening,
   wherein said filter core is provided in said water compartment for communicating with said water stored therein, said filter core comprising a filter casing and a plurality of filter elements received in said filter casing, said filter casing having a plurality of communicating slots for communicating said filter elements with said water received in said water compartment,
   wherein said filter casing is configured to have a ring-shaped structure having a peripheral housing portion and a central opening, said filter elements are accommodated in said peripheral housing portion, said communicating slots being formed on said peripheral housing portion,
   wherein said electrode arrangement of said hydrogen water generator comprises a positive electrode plate and a negative electrode plate provided underneath said filter core at a position corresponding to said central opening of said filter casing, said positive electrode plate and said negative electrode plate being electrically connected to a positive terminal and a negative terminal of a power source respectively so that said positive electrode plate and said negative electrode plate form a positive terminal and a negative terminal respectively for electrolyzing said water in said water compartment,
   wherein each of said positive electrode plate and said negative electrode plate has a circular peripheral shape and has a plurality of through meshes formed thereon for allowing water to pass through said corresponding positive electrode plate and said negative electrode plate,
   wherein said electrode arrangement further comprises an insulating layer and an insulating frame positioned between said positive electrode plate and said negative electrode plate for preventing direct electrical conduction between said positive electrode plate and said negative electrode plate,
   wherein said hydrogen water generator further comprises a carbon cartridge provided underneath said electrode arrangement for facilitating effective electrolysis of said water stored in said water compartment,
   wherein said filter elements comprises, in percentage by weight, 12.5% to 17.7% of maifan stone, 11.3% to 11.8% of diatomaceous earth, 11.3% to 14.5% of active carbon, 11.3% to 11.8% of aluminum oxide, 9.7% to 14.5% of potassium phosphate, 9.2% to 11.3% of palm fiber, 11.85% to 14.5% of ammonium sulfate, and 12.9% to 13.8% of silk fiber.

2. The hydrogen-enriched water generator and dispenser, as recited in claim 1, wherein said main casing has a flat bottom surface for stably resting on an external flat surface so as to form a self-contained unit to generate hydrogen-enriched water.

* * * * *